(12) United States Patent
Kim et al.

(10) Patent No.: US 7,741,105 B2
(45) Date of Patent: Jun. 22, 2010

(54) BIOMOLECULE CHIP AND FABRICATION METHOD THEREOF

(75) Inventors: Young-il Kim, Suwon-si (KR);
Moon-chul Lee, Yongin-si (KR);
Jung-ho Kang, Suwon-si (KR); Tae-sik Park, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 1051 days.

(21) Appl. No.: 11/329,240

(22) Filed: Jan. 10, 2006

(65) Prior Publication Data

US 2006/0154242 A1 Jul. 13, 2006

(30) Foreign Application Priority Data

Jan. 10, 2005 (KR) .................. 10-2005-0002017

(51) Int. Cl.
*B81B 7/04* (2006.01)
(52) U.S. Cl. .................. 435/287.2; 435/4; 436/517; 257/686
(58) Field of Classification Search .................. None
See application file for complete search history.

(56) References Cited

U.S. PATENT DOCUMENTS

2003/0190632 A1* 10/2003 Sosnowski et al. ............. 435/6

FOREIGN PATENT DOCUMENTS

| KR | 1020030027379 | 4/2003 |
| KR | 1020030088782 | 11/2003 |

* cited by examiner

*Primary Examiner*—Anish Gupta
(74) *Attorney, Agent, or Firm*—Cantor Colburn LLP

(57) ABSTRACT

Disclosed is a biomolecule chip and a fabrication method thereof. The biomolecule chip of the invention includes: a substrate; an insulating layer formed on the substrate; an adhesive layer formed on the insulating layer; a seed layer formed on the adhesive layer; an opening patterned at a predetermined location within the adhesive layer, the seed layer and the electroplating layer; and a biomolecule immobilized layer formed on the electroplating layer, the electroplating layer comprising a plasma-treated electroplating layer prior to the formation of the biomolecule immobilized layer. Accordingly, the immobilization of biomolecules onto the surface can be done more effectively by modifying the surface of the substrate in favor of biomolecules.

11 Claims, 9 Drawing Sheets

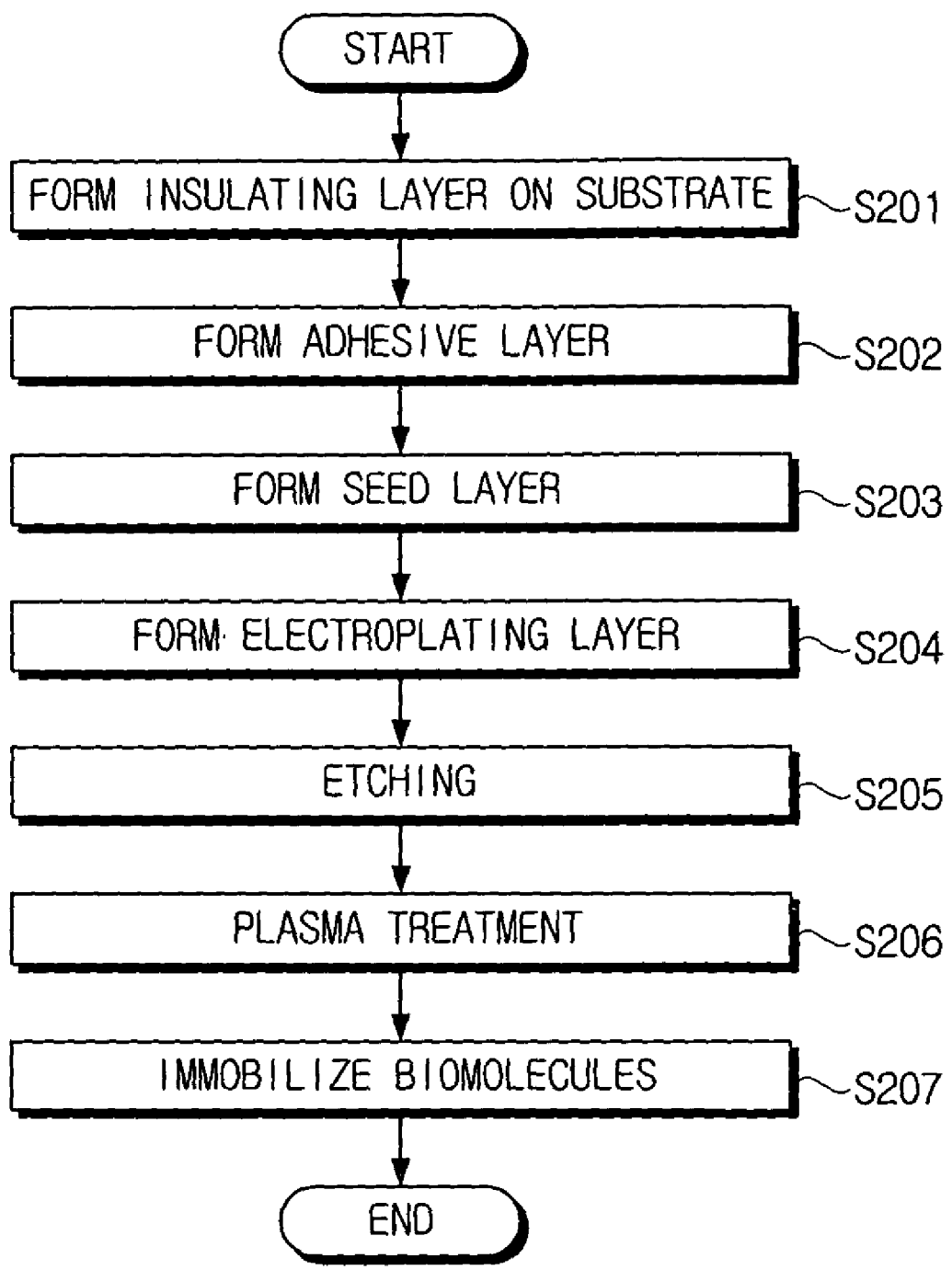

ANGLE : 80.91°

ANGLE : 47.75°

ANGLE : 39.28°

ANGLE : 67.43°

ANGLE : 68.25°

BIOMOLECULE CHIP AND FABRICATION METHOD THEREOF

This application claims priority under 35 U.S.C. §119 to Korean Patent Application No. 2005-02017, filed on Jan. 10, 2005, the entire content of which is incorporated herein by reference.

BACKGROUND OF THE INVENTION

1. Field of the Invention

The present invention relates in general to a biomolecule chip and a fabrication method thereof. More specifically, the present invention relates to a biomolecule chip and a fabrication method thereof based on Micro-Electro-Mechanical Systems (MEMS) technology, in which the surface of a substrate undergoes a special treatment to facilitate the immobilization of biomolecules thereon.

2. Description of the Related Art

A biomolecule chip is a biological microchip comprising a substrate and biomolecules immobilized on the substrate. Biomolecule chips are often categorized based on the type of biomolecules immobilized on the substrate, for example DNA chips, protein chips, and the like. A biomolecule which is immobilized on a chip and binds with a target biomolecule in a sample for analysis is called a probe. Biomolecule chip-related technical fields for further development include biomolecule immobilization techniques for immobilizing biomolecules on a substrate, binding techniques for binding immobilized biomolecules on a biomolecule chip with a sample, biomolecule detection techniques for detecting the existence and the identity of biomolecules based on the analysis of a biomolecule chip on which unknown biomolecules are immobilized.

Depending on the immobilization pattern of a probe, biomolecule chips can be categorized into microarray chips which have probes immobilized on a solid substrate, and lab-on-a-chips which have probes immobilized on a micro channel.

A recent trend in fabrication technology of biomolecule chips is toward using MEMS technology. When a biomolecule chip is fabricated based on MEMS technology, a functional layer is first formed on the substrate, and then biomolecules are immobilized on the substrate. Considering that many biomolecule chip-related applications must have a platform function, an insulating layer is preferably layered on the substrate of the biomolecule chip. Even though most of the materials used for the insulating layer are hydrophobic, biomolecules immobilized on the biomolecule chip are mostly hydrophilic. This difference often makes it difficult to immobilize the biomolecules on the insulating layer. Therefore, to facilitate immobilization of biomolecules on an insulating layer, it is desirable to develop a surface treatment technology for changing a portion of the surface of the insulating layer in contact with biomolecules to be hydrophilic.

SUMMARY OF THE INVENTION

It is, therefore, an object of the present invention is to provide a biomolecule chip and its fabrication method based on MEMS technology, in which the top surface of a substrate undergoes a special treatment to facilitate the immobilization of biomolecules thereon.

To achieve the above and other objects and advantages, there is provided a biomolecule chip comprising: a substrate; an insulating layer formed on the substrate; an adhesive layer formed on the insulating layer; a seed layer formed on the adhesive layer; an electroplating layer being on the seed layer; an opening patterned at a predetermined location within the adhesive layer, the seed layer and the electroplating layer; and a biomolecule immobilized layer being formed on the electroplating layer, the electroplating layer comprising a plasma-treated electroplating layer prior to the formation of the biomolecule immobilized layer.

In an exemplary embodiment, the insulating layer comprises a low dielectric constant (low-k) material selected from the group consisting of: epoxy resin, bis(benzocyclobutene), polyimide, silicon rubber and combinations thereof. Preferably, the insulating layer comprises bis(benzocyclobutene).

In an exemplary embodiment, the adhesive layer comprises: titanium, chrome, tungsten, tantalum, tantalum nitrides and combinations thereof.

In an exemplary embodiment, the seed layer comprises a metal selected from the group consisting of copper and silver.

In an exemplary embodiment, the biomolecules are selected from the group consisting of: antigens, antibodies, nucleotides, enzymes, bacteria, yeasts, mycobacteria, virus, bacterial pili, bacteria flagella substances, nucleic acid, polysaccharides, lipids, proteins, carbohydrates, hormones, cofactors and cells.

In an exemplary embodiment, the plasma treatment is preferably carried out under a gas atmosphere, the gas being selected from the group consisting of: oxygen, fluorine, argon, chlorine and mixtures of at least two of these gases. More preferably, the plasma treatment is carried out under a mixed gas (oxygen+fluorine) atmosphere.

In an exemplary embodiment, the substrate is made of a solid material selected from the group consisting of: silicon wafer, glass, quartz, ceramic, metals and plastic.

Another aspect of the present invention provides a fabrication method of a biomolecule chip, the method comprising: forming an insulating layer on a substrate; forming an adhesive layer on the insulating layer; forming a seed layer on the adhesive layer; arraying an etching mask on the seed layer for patterning; electroplating the upper portion of the etching mask; removing the etching mask, etching the exposed seed layer and the adhesive layer below and thereby, forming a hole that exposes a predetermined area of the insulating layer; carrying out a plasma treatment on the electroplating layer and the upper portion of the exposed insulating layer; and immobilizing biomolecules on the plasma treated surface.

The method may further comprise: before the plasma treatment, treating the electroplating layer with a thiol compound.

The method may further comprise: before immobilizing biomolecules, treating the plasma treated surface with a basic substance.

In another embodiment, the insulating layer comprises a low dielectric constant (low-k) material selected from the group consisting of: epoxy resin, bis(benzocyclobutene), polyimide and silicon rubber. Preferably, the insulating layer comprises bis(benzocyclobutene).

In another embodiment, the adhesive layer comprises a metal selected from the group consisting of: titanium, chrome, tungsten, tantalum and tantalum nitrides.

In another embodiment, the seed layer comprises copper and silver.

In another embodiment, the biomolecules are selected from the group consisting of: antigens, antibodies, nucleotides, enzymes, bacteria, yeasts, mycobacteria, virus, bacterial pili, bacterial flagella substances, nucleic acid, polysaccharides, lipids, proteins, carbohydrates, hormones, cofactors and cells.

In another embodiment, the plasma treatment is carried out under a gas atmosphere, the gas being selected from the group consisting of: oxygen, fluorine, argon, chlorine and mixtures of at least two of these gases. Preferably, the plasma treatment is carried out under a mixed gas (oxygen+fluorine) atmosphere.

In another embodiment, the substrate comprises a solid material selected from the group consisting of: silicon wafer, glass, quartz, ceramic, metals and plastic.

In another embodiment, the plasma treatment comprises an RIE (reactive ion etching) method or ashing method.

In another embodiment, the etching mask is selected from the group consisting of: photosensitive polymer, metal hard mask, $SiO_2$, poly silicon and silicon nitride. Preferably, the photosensitive polymer is a photoresist.

In another embodiment, the biomolecules are immobilized by inkjetting or spotting a biomolecule-containing solution over the surface of the substrate, or by immersing the substrate directly into a biomolecule-containing solution.

BRIEF DESCRIPTION OF THE DRAWINGS

The above aspects and features of the present invention will be more apparent by illustrating certain preferred embodiments of the present invention with reference to the accompanying drawings, in which:

FIG. 2 is a flow chart schematically describing a fabrication method of a biomolecule chip according to the present invention;

DETAILED DESCRIPTION OF THE INVENTION

Figure 1:
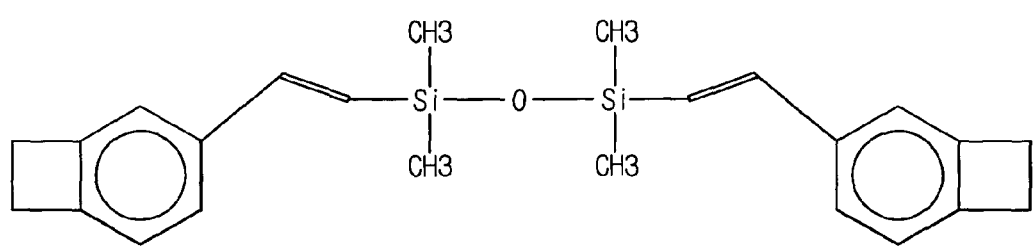
FIG. 1 illustrates a chemical formula for an insulating layer used in the fabrication of a biomolecule chip in accordance with an embodiment of the present invention.
Figure 1A:
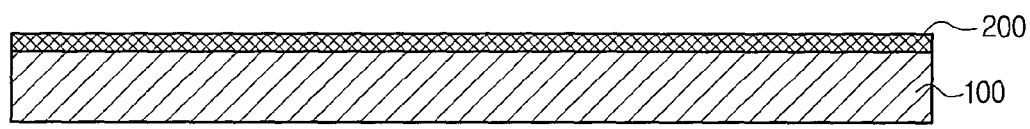
FIGS. 1A to 1E are cross-sectional views schematically showing a fabrication method of a biomolecule chip, according to the present invention.
Figure 1B:
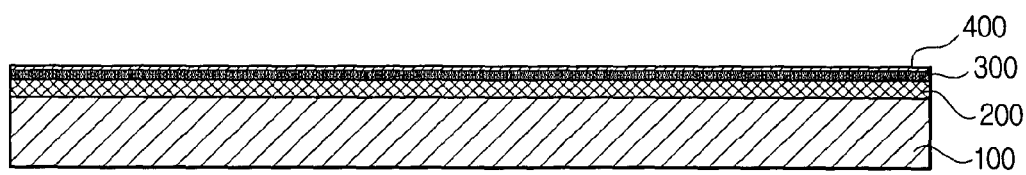
Figure 1C:
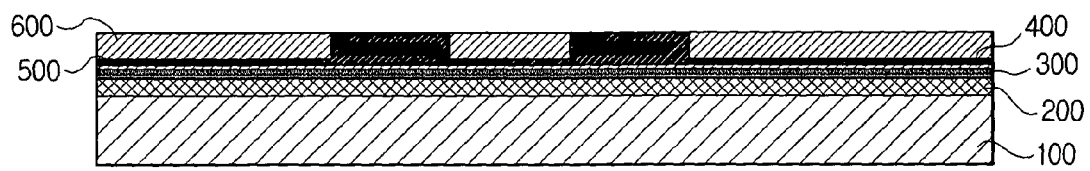
Figure 1D:
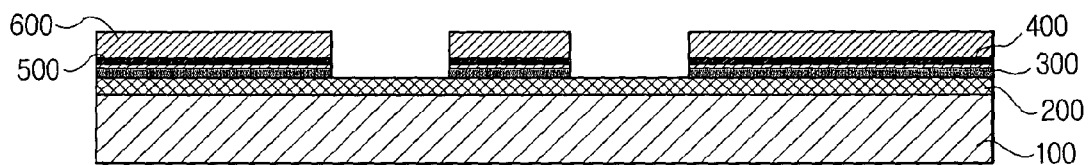
Figure 1E:
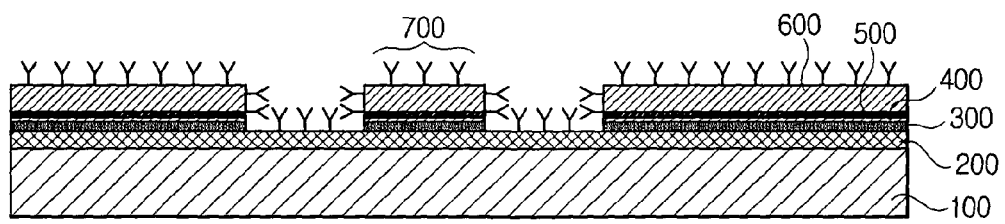

An exemplary embodiment of the present invention will be described herein below with reference to the accompanying drawings. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

In the following description, the same drawing reference numerals are used to denote the same elements throughout. As used herein, the term "and/or" includes any and all combinations of one or more of the associated listed items. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

FIGS. 1A to 1E are cross-sectional views schematically showing a fabrication method of a biomolecule chip according to the present invention, and FIG. 2 is a flow chart describing the fabrication method of a biomolecule chip according to the present invention.

Referring generally to FIGS. 1A through 1E and FIG. 2, an insulating layer 200 is formed on the top of a substrate 100 (S201 of FIG. 2). The insulating layer 200 is formed for the platform function of the biomolecule chip.

The substrate 100 includes a solid plate made, for example, from silicon wafer, glass, quartz, ceramic, metals or plastic. These exemplary substrate materials are provided for illustrative purposes only, and the present invention is not limited thereto.

The insulating layer 200 includes a low dielectric constant (low-k) material. Examples of low-k materials include, but are not limited to, epoxy resin, bis(benzocyclobutene), polyimide and silicon rubber.

Examples of commercially available low-k materials include Ajinomoto buildup film (ABF, epoxy resin) manufactured by Ajinomoto Inc., BCB (bis (benzocyclobutene)) manufactured by Dow chemical company, DC6812 (silicon rubber) manufactured by Dow Corning corporation, silk manufactured by Dow chemical company, and IN manufactured by Ibidem company.

Preferably, bis(benzocyclobutene) having the structure shown in Chemical Formula 1 below (as well as in FIG. 1) is used for the insulating layer. Due to its high solvent resistance for any type of solvents (including acids or bases), as well as its low dielectric constant, bis(benzocyclobutene) is commonly used in biomolecule chip-related fields.

[Chemical Formula 1]

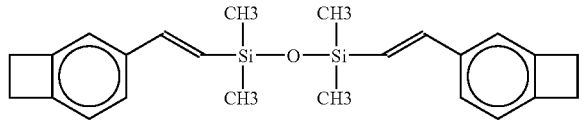

As shown above and in FIG. 1, bis(benzocyclobutene) is a nonpolar, aromatic cyclic compound having a symmetrically located pair of benzocyclobutenes. Because of the structural characteristics of bis(benzocyclobutene), the compound is hydrophobic; that is, it is not miscible with water which is a polar compound. The hydrophobic characteristic of bis(benzocyclobutene) makes it very difficult to immobilize hydrophilic biomolecules on the top of the insulating layer.

Any known methods in the related art may be utilized to form the insulating layer 200 on the substrate. Such methods include, for example, spin coating methods, PECVD (Plasma Enhanced Chemical Vapor Deposition) methods, SAM (Self Assembled Monolayer), evaporation or immersion. Preferably, a spin coating method is used.

The insulating layer 200 has a thickness on the order of several micrometers. For example, the thickness of the insulating layer 200 is in a range from about 3 μm to about 8 μm and, more preferably, from about 4 μm to about 6 μm.

In the present embodiment, an adhesive layer 300 is formed on the insulating layer (S202 of FIG. 2). The adhesive layer 300 improves the adhesion of a metal that is subsequently deposited thereon. Examples of materials for use in the adhesive layer 300 include titanium, chrome, tungsten, tantalum and tantalum nitrides, although the present invention is not limited thereto. In some embodiments, the adhesive layer 300 also includes titanium or chrome.

Then, a seed layer 400 is deposited on the adhesive layer 300 (S203 of FIG. 2). The seed layer 400 functions as an electrical connector for the edges of the substrate 100. In general, copper or silver may be used for the seed layer 400.

After the seed layer 400 is deposited, an etching mask 500 is positioned for patterning. Examples of materials for the etching mask include photosensitive polymer, metal hard mask, $SiO_2$, poly silicon or silicon nitride, although the present invention is not limited thereto. In certain embodiments, the etching mask includes a photosensitive polymer comprising a photoresist composition.

Following the patterning through the etching mask 500, an electroplating layer 600 is formed (S204 of FIG. 2), and an exposed area formed by the patterning is etched (S205 of FIG. 2).

In certain embodiments, an electroplating mold is formed before forming the electroplating layer.

An exemplary material for use in the electroplating layer 600 is copper, although the present invention is not limited thereto.

There are generally two types of etching methods known in the art: wet etching and dry etching. According to the wet etching method, the adhesive layer 300 and the seed layer 400 are dissolved and etched in an etching solution through a patterned portion of the etching mask material. Examples of compounds for the etching solution include $H_2SO_4$, $H_3PO_4$, $H_2O_2$, HF, HCl and $NH_4OH$. In the dry etching method, the etching is performed by using a gas, primarily plasma. Well-known dry etching methods include, for example, RIE (reactive ion etching) and ashing. The adhesive layer 300 and the seed layer 400 may thus be etched using a plasma under an oxygen or an inert gas atmosphere.

As a result of the etching (S205 of FIG. 2), the insulating layer 200 at the patterned area is exposed. Although the surface of the electroplating layer 600 is easily modified to be hydrophilic through treatment with a thiol compound, the surface of the insulating layer 200 is not easily modified by the thiol compound treatment. Therefore, in fabricating a biomolecule chip according to the present invention embodiments, the exposed surface of the insulating layer 200 is modified to be hydrophilic through a plasma treatment (S206).

In effect, the plasma treatment is very similar to the dry etching method. For instance, the plasma treatment for modifying the exposed surface of the insulating layer 200 is based on RIE or ashing. Examples of a gas for use in the plasma treatment include oxygen, fluorine, argon, chlorine and mixtures of at least two of these gases. Preferably, oxygen or fluorine is used, and more preferably, a mixture of oxygen and fluorine is used.

When the plasma treatment is carried out under oxygen atmosphere, $CH_3$ and C shown in Chemical Formula 1 are attacked, and —OH (hydroxyl) is formed. When a mixture of oxygen and fluorine is used, both the oxygen (O) between Si and Si and the $CH_3$ react, forming more —OH (hydroxyls) on the surface of the substrate. In other words, when using oxygen only, although the oxygen chemically reacts with C to a certain degree, its chemical reactivity with the Si—O bond is relatively weak. Thus, to form —OH by breaking the Si—O bond, it is preferable to add fluorine and perform the plasma treatment under the mixed gas atmosphere.

Here, fluorine can be provided in the form of $SF_6$ or $CH_4$, although it should be appreciated that these are provided for illustrative purposes only.

Different voltages are applied to the plasma treatment for etching and for surface modification, respectively. In this manner, the treatment intensity can be adjusted differentially.

As a result of the plasma treatment, the bis(benzocyclobutene) of the insulating layer breaks down, forming many hydroxyls (—OH) on the surface of the insulating layer, resulting in a hydrophilic insulating layer.

Next, the substrate is treated in the presence of a base, so that oxide anions, which are aggressive in bonding with biomolecules, can be formed on the surface of the substrate. In this manner, biomolecules are more easily immobilized onto the substrate.

Once the surface of the substrate is modified through the plasma treatment, biomolecules 700 are immobilized thereon, and the fabrication of the biomolecule chip is completed (S207 of FIG. 2).

Diverse biomolecules can be immobilized, depending on the application field. For example, frequently used biomolecules are selected from antigens, antibodies, nucleotides, enzymes, bacteria, yeasts, mycobacteria, viruses, bacterial pilis, bacterial flagella substances, nucleic acid, polysaccharide, lipid, protein, carbohydrate, hormone, cofactor and cell, but these are provided for illustrative purposes only.

The biomolecules can be immobilized by inkjetting/spotting a biomolecule-containing solution on the modified surface of the substrate, or the substrate can be immersed directly into a biomolecule-containing solution.

The following will now describe examples of the present invention. However, these examples are provided for illustrative purposes only, and the claims of the invention are not limited thereto.

EXAMPLES

Example 1

A 4-inch thick silicon wafer was spin coated with bis (benzocyclobutene) to form an insulating layer. The thickness of the insulating layer was 4 μm. Titanium was deposited on top of the insulating layer by electron beam deposition to form an adhesive layer, and then copper was deposited on top of the adhesive layer by electron beam deposition to form a seed layer.

Next, a photoresist was positioned on top of the seed layer for patterning, and an electroplating layer made of copper was formed thereon.

Under an oxygen atmosphere, the photoresist, the patterned adhesive layer, and the seed layer were then removed by means of an ashing machine.

The prepared substrate went through a surface treatment with a thiol compound, to form hydroxyls on the surface of the copper layer. In this manner, the surface of the substrate was modified from being hydrophobic to being hydrophilic.

After that, a plasma treatment based on the RIE method was carried out. At this time, a mixture of $O_2$ and $SF_6$ was injected; $O_2$ was provided at an injection speed of 40 sccm and $SF_6$ was provided at an injection speed of 10 sccm, respectively. Here, 'sccm' is an abbreviation of standard cubic centimeter per minute, and indicates a flow speed of 1 cc/minute. The plasma treatment was conducted at 100 mtorr pressure and 200 W voltage for 30 seconds.

Then, the surface characteristics of the substrate of the biomolecule chip were tested to verify the transformation to hydrophilic. Lastly, glucose oxidase was immobilized onto the substrate through the immersion method.

Example 2

A biomolecule chip was fabricated in the same way as described in Example 1, except that the plasma treatment was carried out for 60 seconds.

Example 3

A biomolecule chip was fabricated in the same way as described in Example 1, except that the plasma treatment was carried out for 90 seconds.

Example 4

A biomolecule chip was fabricated in the same way as described in Example 1, except that only oxygen ($O_2$) was injected at 40 sccm during the plasma treatment.

Example 5

A biomolecule chip was fabricated in the same way as described in Example 4, except that the plasma treatment was carried out for 60 seconds.

Comparative Example

A biomolecule chip was fabricated in the same way as described in Example 1, except that the RIE method was not used for the plasma treatment.

{Tests}

The surface characteristics of the substrates for each of the biomolecule chips obtained in Examples 1 through 5, and the Comparative Example were tested. It should be noted that the test was conducted before the biomolecules were immobilized onto the substrates. Test results were then compared.

FTIR-ATR

Hydroxyls on the surface of each substrate were monitored by FTIR-ATR (Fourier Transform Infra Red/Attenuated Total Reflectance) to make sure that the surface of the substrate was modified to be hydrophilic.

Figure 3A:
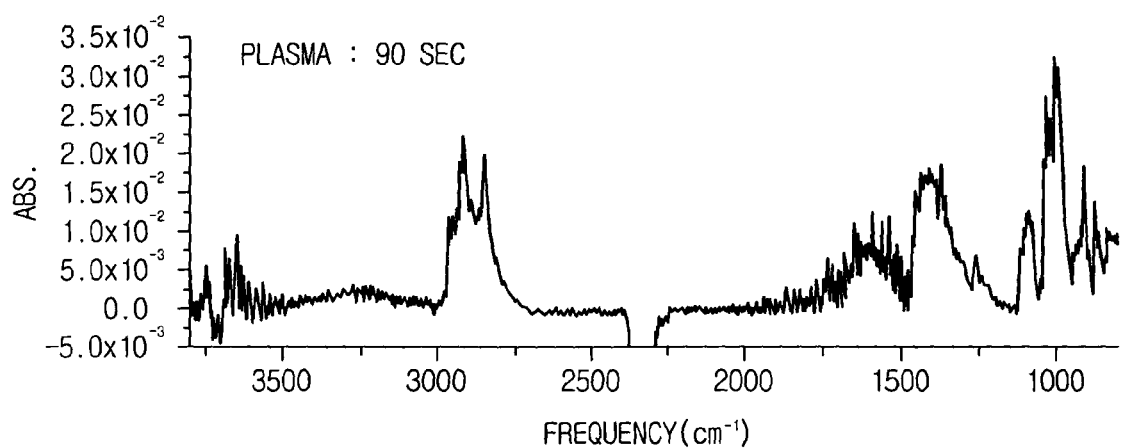
FIGS. 3A to 3B illustrate changes in a surface characteristic of a biomolecule chip that is fabricated according to the present invention.
Figure 3B:
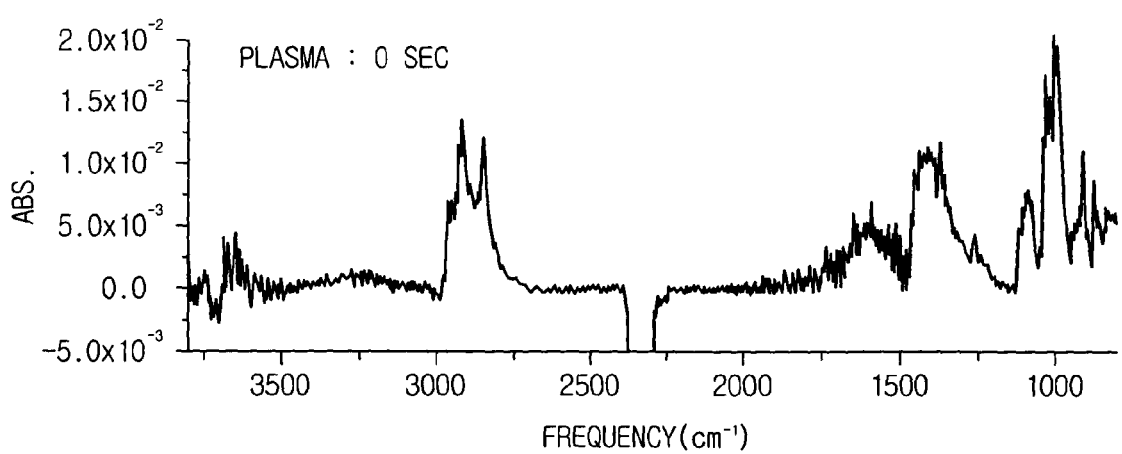

FIGS. 3A to 3B graphically illustrate the surface characteristics of the surface of the substrates obtained from Example 3 and Comparative Example, respectively. Here, the changes in surface characteristics were measured by FT-IR.

FIG. 3A illustrates an FT-IR graph showing surface characteristics of the substrate after the plasma (surface) treatment for 90 seconds under oxygen and fluorine atmosphere (i.e., Example 3). FIG. 3B illustrates an FT-IR graph showing surface characteristics of the substrate where no plasma (surface) treatment was performed (i.e., Comparative Example).

In each graph, the y-axis represents absorbance, and the x-axis represents frequency.

A hydroxyl group is an O—H group; the frequency of —OH in the infrared spectroscopy is in a broad range from about $3000^{-1}$ to $3500^{-1}$ cm.

As can be seen in FIG. 3A, a broad absorption peak was observed at the corresponding frequency for the hydroxyl groups. This indicates the presence of hydroxyl groups on the surface of the substrate obtained from Example 3, modifying the hydrophobic surface of the substrate to be hydrophilic. In contrast, in FIG. 3B, no absorption peak was observed at the corresponding frequency for the hydroxyl group. This means that hydroxyl groups are not present on the surface of the substrate obtained from the Comparative Example.

Observation of Water Contact Angle

For this test, a small drop of water was dripped on each substrate, and the contact angle between the substrate and the water was measured. This test is to identify the relation between the degree of hydrophilicity and the area of water spread. According to the test result, the greater the degree of hydrophilicity, the bigger the area of water spread, which means that the water contact angle becomes smaller. It was observed that the surface of the substrate was hydrophilic when its water contact angle was smaller than about 50 degrees.

FIGS. 4A to 4E illustrate the measurements of water contact angles on the surface of the substrates obtained from Comparative Example, Example 1, Example 2, Example 4 and Example 5, respectively.

Figure 4A:
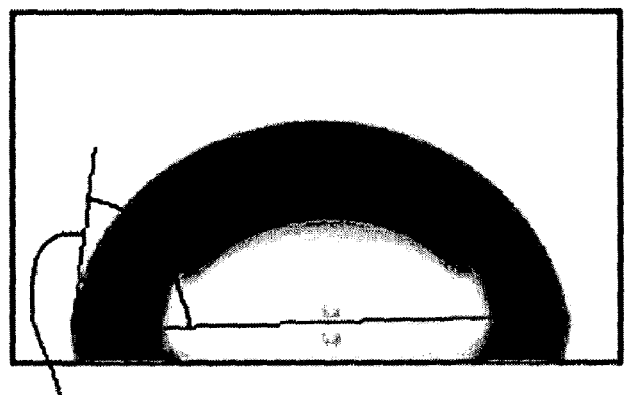
FIGS. 4A to 4E illustrate different surface contact angles over time of a biomolecule chip that is fabricated according to the present invention.

As can be seen in FIG. 4A, the water contact angle of the surface of the substrate with no plasma treatment was 80.91°, meaning that the surface of the substrate remained hydrophobic.

Figure 4B:
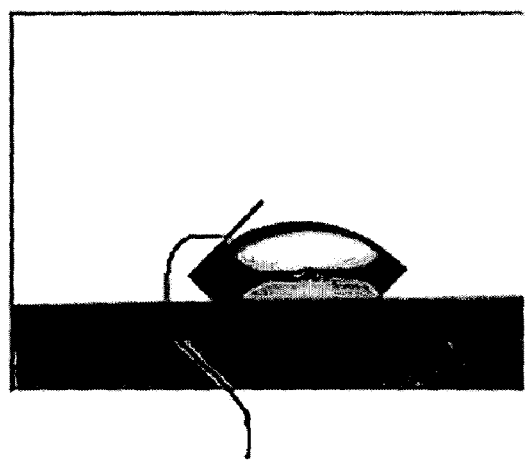
Figure 4C:
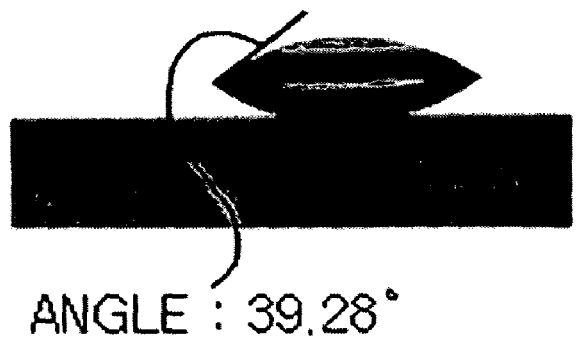
Figure 4D:
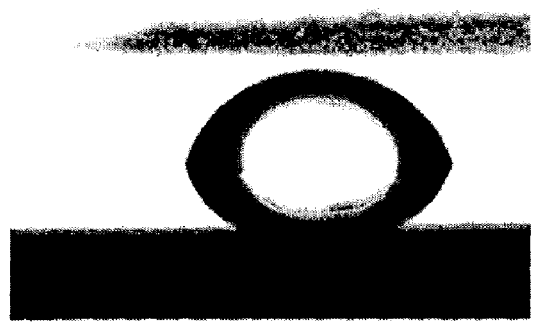
Figure 4E:
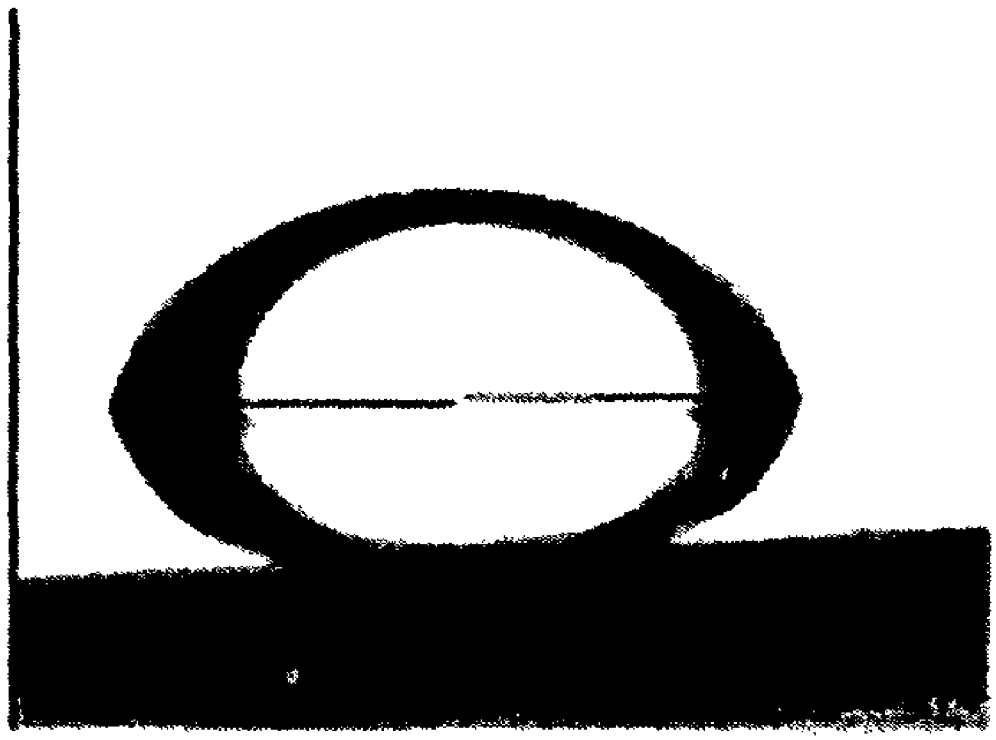

On the other hand, as shown in FIGS. 4B and 4C, the water contact angle of the surface of the substrates from Example 1 and 2 was 47.75° and 39.28°, respectively. Therefore, the surfaces of the substrates from both examples were hydrophilic. Furthermore, the water contact angle of the surface of the substrates from Example 4 and 5 was 67.43° and 68.25°, respectively. Therefore, the surfaces of these substrates are not sufficiently hydrophilic.

These results show that the substrate of the biomolecule chip can be modified to be hydrophilic more effectively if the plasma treatment is conducted under a mixed gas (oxygen and fluorine) atmosphere.

XPS (X-Ray Photoelectron Spectroscopy)

The ratio of the relative bonding energy of $O_{1s}$ to $C_{1s}$ was measured. It was observed that other bonds with O disappeared, whereas O was exposed more frequently.

Figure 5:
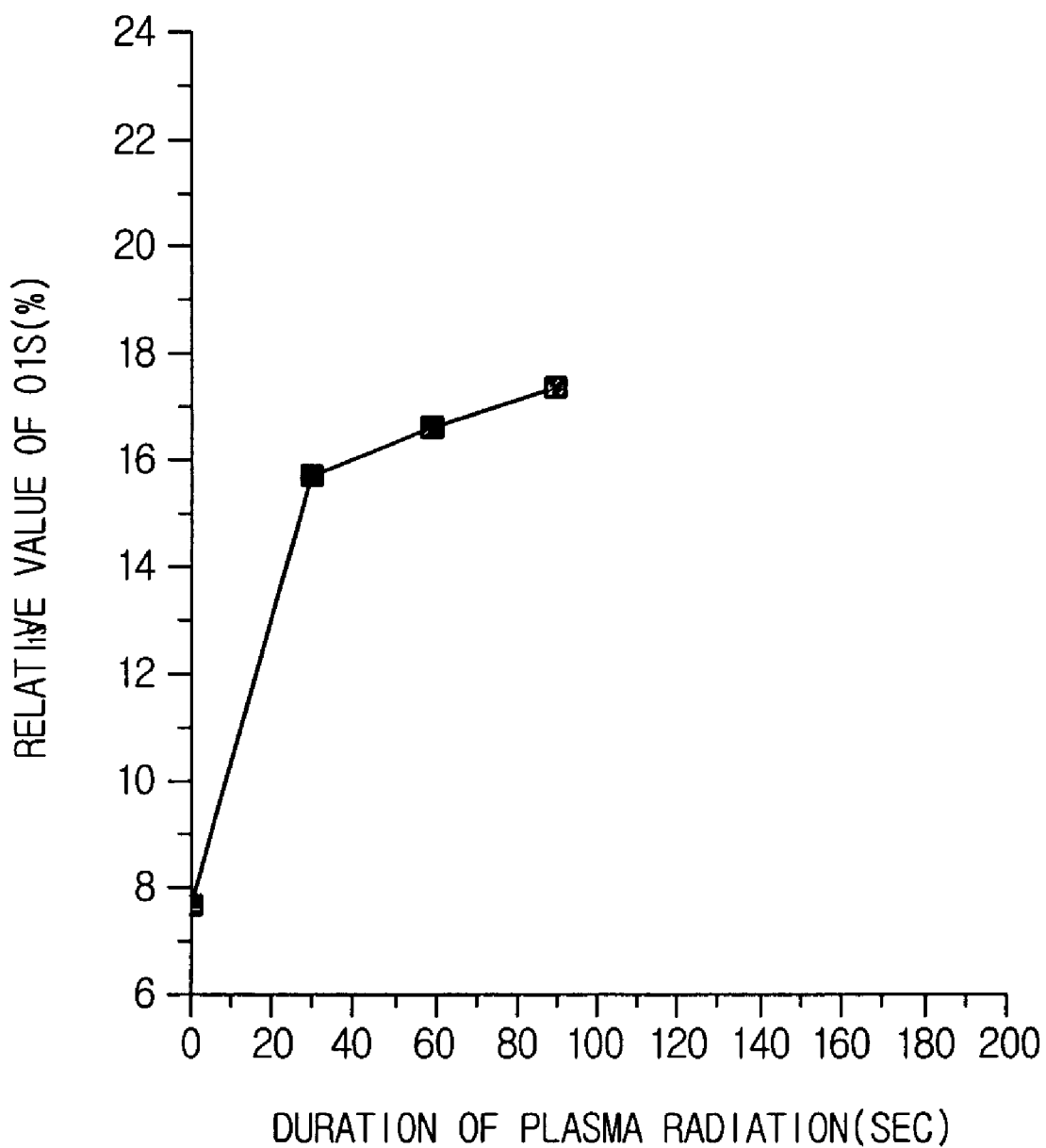
FIG. 5 is an X-ray photoelectron spectroscopy graph illustrating a relationship between $O_{1s}$ and the duration of plasma radiation.
Figure 6:
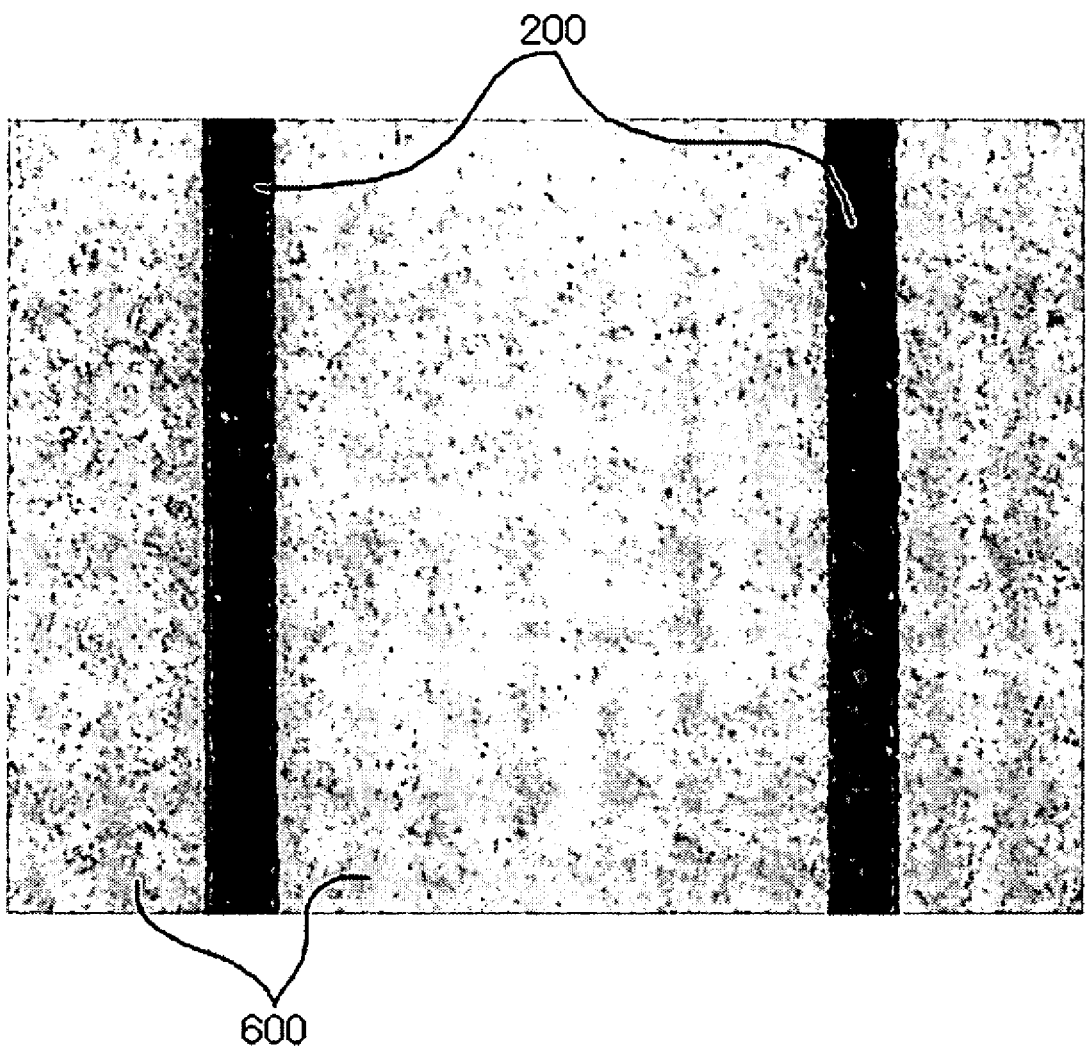
FIG. 6 is a planar projection print of a biomolecule chip that is fabricated according to the present invention.

FIG. 5 is an X-ray photoelectron spectroscopy graph illustrating the relation between a relative value of $O_{1s}$ (y-axis) in percentage and the duration of plasma radiation (x-axis).

Table 1 provides specific numerical values from the graph.

TABLE 1

| Description | Comparative Example | Example 1 | Example 2 | Example 3 |
|---|---|---|---|---|
| Value (%) | 7.66 | 15.65 | 16.56 | 17.26 |

As can be seen in FIG. 5 and Table 1, the relative bonding energy value of $O_{1s}$ was small in the case of the Comparative Example without the plasma treatment, but the relative bonding energy value of $O_{1s}$ for each of Examples 1, 2 and 3 was large. This indicates that the Si—O bond in the bis(benzycyclobutene) (please refer to Chemical Formula 1) was broken by the plasma treatment, and the O became an anion. As such, the plasma-treated surface of the substrate was modified to be hydrophilic.

From these test results, it can be inferred that only the plasma-treated surface of the biomolecule chip (e.g., Example 1, 2 and 3) was modified to be hydrophilic, whereas the surface of the biomolecule chip from the Comparative Example for which no plasma treatment was carried out remained hydrophobic. Moreover, the degree of hydrophilicity of the surface was greater when the plasma treatment was carried out under the mixed gas (oxygen and fluorine) atmosphere (e.g., Example 1, 2 and 3) than under the oxygen gas atmosphere only (e.g., Example 4 and 5).

As described above, the biomolecule chip and its fabrication method of the present invention can provide a biomolecule chip whose biomolecule immobilization is improved with surface modification of the substrate.

The foregoing embodiments and advantages are merely illustrative and are not to be construed as limiting the present invention. The present teaching can be readily applied to other types of apparatuses. Also, the description of the embodiments of the present invention is intended to be illustrative, and not to limit the scope of the claims, and many changes, modifications, and variations will be apparent to those skilled in the art. Such changes, modification and variations should not be construed as departing from the spirit or scope of the present invention

What is claimed is:

1. A biomolecule chip, comprising:
   a substrate;
   an insulating layer formed on the substrate, wherein the insulating layer comprises a low dielectric constant (low-k) material;
   an adhesive layer formed on the insulating layer;
   a seed layer formed on the adhesive layer;
   an electroplating layer formed on the seed layer;
   an opening patterned at a predetermined location within the adhesive layer, the seed layer and the electroplating layer; and
   a biomolecule immobilized layer formed on the electroplating layer and the insulating layer exposed by the opening, the electroplating layer comprising a plasma-treated electroplating layer, and the insulating layer exposed by the opening comprising a plasma-treated insulating layer, where plasma treating is prior to the formation of the biomolecule immobilized layer.

2. The biomolecule chip according to claim 1, wherein the low dielectric constant (low-k) material is selected from the group consisting of: epoxy resin, bis(benzocyclobutene), polyimide and silicon rubber.

3. The biomolecule chip according to claim 2, wherein the insulating layer comprises bis(benzocyclobutene).

4. The biomolecule chip according to claim 1, wherein the adhesive layer comprises a metal selected from the group consisting of: titanium, chrome, tungsten, tantalum and tantalum nitrides.

5. The biomolecule chip according to claim 1, wherein the seed layer comprises one or more of copper and silver.

6. The biomolecule chip according to claim 1, wherein the biomolecules are selected from the group consisting of: antigens, antibodies, nucleotides, enzymes, bacteria, yeasts, mycobacteria, virus, bacterial pili, bacterial flagella substance, nucleic acids, polysaccharides, lipids, proteins, carbohydrates, hormones, cofactors and cells.

7. The biomolecule chip according to claim 1, wherein the plasma treatment is carried out under gas atmosphere, the gas being selected from the group consisting of: oxygen, fluorine, argon, chlorine and mixtures of at least two or more thereof.

8. The biomolecule chip according to claim 7, wherein the plasma treatment is carried out under a mixed gas atmosphere consisting of oxygen and fluorine.

9. The biomolecule chip according to claim 1, wherein the substrate is made of a solid material selected from the group consisting of: silicon wafer, glass, quartz, ceramic, metals and plastic.

10. The biomolecule chip according to claim 1, wherein the substrate is made of a silicon wafer, the insulating layer comprises bis(benzocyclobutene), the adhesive layer comprises titanium, and the seed layer comprises copper.

11. The method according to claim 1, wherein the substrate is made of a silicon wafer, the insulating layer comprises bis(benzocyclobutene), the adhesive layer comprises titanium, and the seed layer comprises copper.

* * * * *